(12) United States Patent
Witz et al.

(10) Patent No.: US 8,638,432 B2
(45) Date of Patent: Jan. 28, 2014

(54) METHODS OF USING LASER OPTICAL DEVICES

(75) Inventors: Gregoire Witz, Birmenstorf (CH); Hans-Peter Bossmann, Lauchringen (DE)

(73) Assignee: Alstom Technology Ltd., Baden (CH)

( * ) Notice: Subject to any disclaimer, the term of this patent is extended or adjusted under 35 U.S.C. 154(b) by 0 days.

(21) Appl. No.: 13/413,857

(22) Filed: Mar. 7, 2012

(65) Prior Publication Data

US 2012/0206717 A1    Aug. 16, 2012

Related U.S. Application Data

(63) Continuation of application No. PCT/EP2010/062119, filed on Aug. 19, 2010.

(30) Foreign Application Priority Data

Sep. 10, 2009  (CH) ........................ 1406/09

(51) Int. Cl.
*G01J 3/44* (2006.01)

(52) U.S. Cl.
USPC .......................................... 356/301

(58) Field of Classification Search
USPC ............................ 356/72–73, 301
See application file for complete search history.

(56) References Cited

U.S. PATENT DOCUMENTS

| | | | |
|---|---|---|---|
| 4,030,827 A | 6/1977 | Delhaye et al. | |
| 7,535,565 B1 * | 5/2009 | Viertl et al. | 356/318 |
| 2003/0115941 A1 | 6/2003 | Srivastava et al. | |
| 2007/0134518 A1 | 6/2007 | Feist et al. | |
| 2007/0153268 A1 * | 7/2007 | Panza et al. | 356/301 |

FOREIGN PATENT DOCUMENTS

| | | |
|---|---|---|
| EP | 0552821 | 7/1993 |
| GB | 2330653 | 4/1999 |
| WO | WO2011/029708 | 3/2011 |

OTHER PUBLICATIONS

Search Report for Swiss Patent App. No. 1406/2009 (Nov. 15, 2009).
International Search Report for PCT Patent App. No. PCT/EP2010/062119 (Dec. 6, 2010).

* cited by examiner

*Primary Examiner* — Tarifur Chowdhury
*Assistant Examiner* — Abdullahi Nur
(74) *Attorney, Agent, or Firm* — Buchanan Ingersoll & Rooney PC

(57) ABSTRACT

In a method of spatially detecting the chemical composition of nonmetallic components on a surface which is subsequently to be coated with a metallic and/or ceramic and/or organic layer, a laser optical device is provided. The turbine part is irradiated with monochromatic irradiation at a first wavelength ($\lambda_{in}$) with the laser optical device. Radiation is detected which is emitted by the surface at a second wavelength ($\lambda_{out}$) which is longer than the first wavelength ($\lambda_{in}$).

17 Claims, 1 Drawing Sheet

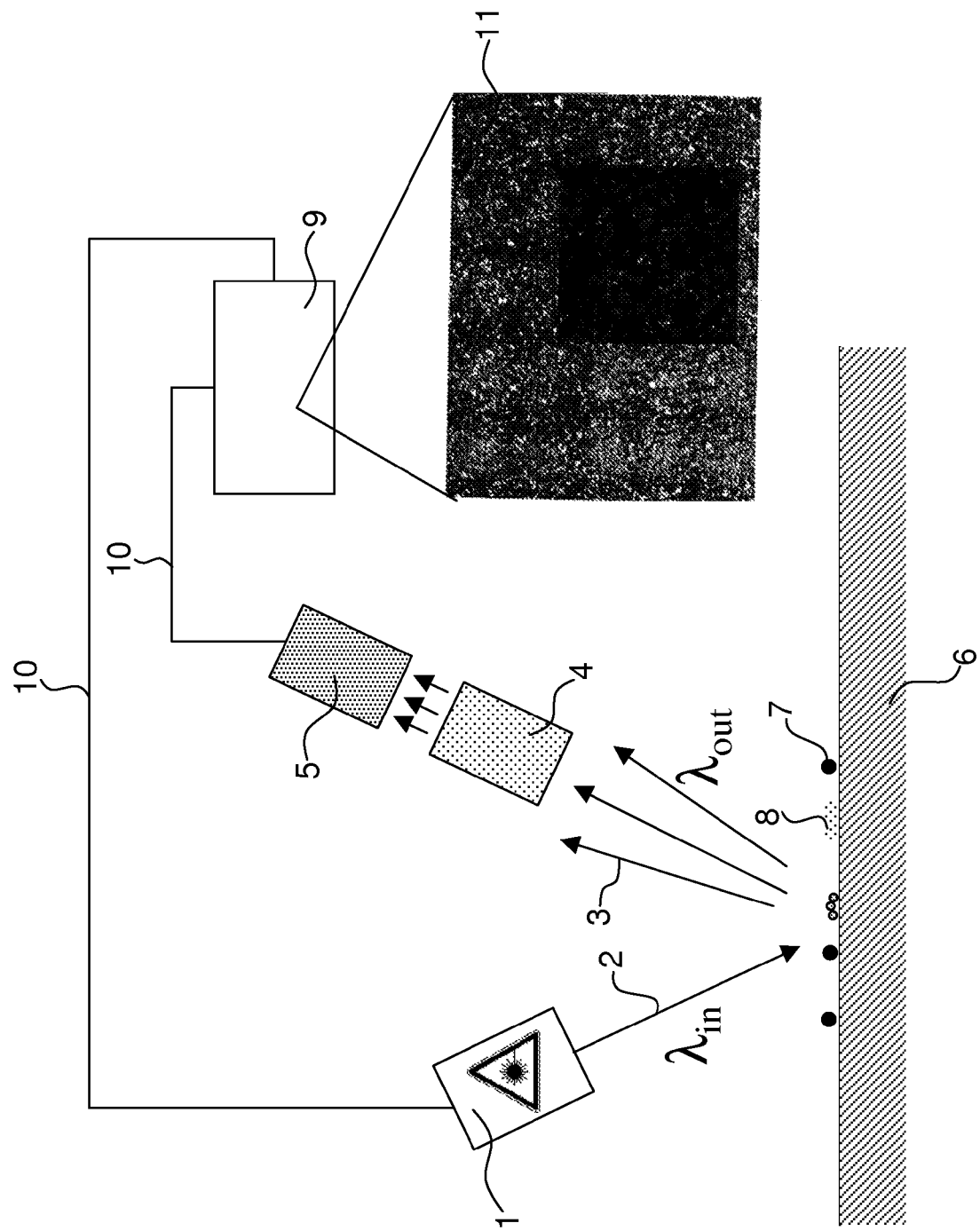

METHODS OF USING LASER OPTICAL DEVICES

This application is a Continuation of, and claims priority under 35 U.S.C. §120 to, International Application No. PCT/EP2010/062119, filed 19 Aug. 2010, and claims priority under 35 U.S.C. §§119, 365 therethrough to Swiss App. No. 01406/09, filed 10 Sep. 2009, the entireties of which are incorporated by reference herein.

BACKGROUND

1. Field of Endeavor

The present invention relates to the use of a laser optical device for optical inspection of the quality of a surface before it is coated with a layer, preferably a metallic, ceramic or organic layer.

2. Brief Description of the Related Art

Insufficient qualities of metallic or ceramic coatings on the surface of gas turbine parts, for example metallic bonding layers of thermal barrier layers, are often attributable to surface contaminations which are due to production or result from processing steps preceding the application of the metallic layer. For example, such surface contaminations may be results of the casting method or forging method, or results of the surface treatment of the unfinished part (for example, sandblasting or cleaning with organic solvents) or undesired contaminations from a previous coating stage. However, they may also simply involve dirt or oxidation products. Such contaminations are typically inspected according to the prior art by metallographic cross sections, pull-off adhesion tests or by scratch tests of the coated parts. All these methods are destructive methods and suffer from the corresponding known disadvantages.

SUMMARY

One of numerous aspects of the present invention includes a new use of a laser optical device, particularly in the scope of a nondestructive method for the quality inspection of surfaces, in particular parts for turbines, for example gas turbines, particularly for surfaces which are subsequently to be coated, for example with a metallic layer, for example as a bonding layer for a thermal protection layer. However, the use also extends to the preparation of other coatings, for example ceramic layers or organic layers. In particular, the proposed uses are intended to make it possible to reliably detect residues of the casting method or forging method, but also from preparatory working steps for the (metallic) coating, for example the residues of surface cleaning or surface structuring by sandblasting, washing, plasma cleaning, etching etc. The intention is that both inorganic and organic contaminations can be determined, regardless of whether they are present point-wise or over an area, and spatial resolution is intended to be possible. Preferably, this essentially involves identifying the nonmetallic components on the surface with respect to their spatial distribution on the surface as well as with respect to their chemical composition.

Another aspect includes the use of a laser optical device with monochromatic irradiation at a first wavelength and detection of the radiation emitted by a surface to be examined with a second wavelength, which is longer than the first wavelength, for spatially resolved analysis of the quality, or degree of contamination, of the surface of a turbine part which is subsequently to be coated with a metallic and/or ceramic and/or organic layer.

In fact, there has not previously been any nondestructive method for inspecting the quality of the preparatory steps before coating of a gas turbine part, quality being intended to mean the suitability of the surface for a subsequent coating step. Typically, quality inspection of the surface includes spatially resolved determination of the chemical composition of nonmetallic components on the surface, since these may potentially interfere with a subsequent coating process. According to principles of the present invention, such a method is proposed as a laser optical method in which the input radiation has a higher energy than that emitted and measured.

Specifically, methods or devices known per se may be used, for example Raman spectrometers (for example in the form of microprobes), such as are described in U.S. Pat. Nos. 4,030,827, 4,586,819, and 5,194,912. Such devices can thus be to examine the surfaces of turbine parts, in particular gas turbine parts, from the production of unfinished parts or after a preparatory treatment of such an unfinished part (a first coating of the unfinished part, which has already been carried out, is likewise possible) and before (optionally further) coating of the surface (metallic and/or ceramic and/or organic layer). The devices as have been described very generally in these documents according to the prior art, but not in connection with such a use, are expressly included in the disclosure content of the present description.

A first embodiment is thus characterized in that the device is a Raman spectrometer (for example as a microprobe). The Raman spectrometer is in this case used for the determination of organic and/or inorganic, in particular nonmetallic, contaminations/residues.

As an alternative or in addition, it may also be a fluorescence spectrometer (for example as a microprobe). For example, devices as have been described in U.S. Pat. No. 4,791,310 can be used for spatially resolved examination. The devices as have been described very generally in this document, but not in connection with such a use, are expressly included in the disclosure content of the present description.

Another embodiment is thus characterized in that the laser optical device is a fluorescence spectrometer. Specifically in connection with the proposed application, it has been found that a fluorescence spectrometer can be used very sensitively for the determination of aluminum oxide on the surface.

According to another preferred embodiment, such a use is characterized in that the device comprises both a Raman spectrometer and a fluorescence spectrometer. In other words, a combined device is used, in which case either individual laser light sources (with equal or different irradiation wavelengths) or a common laser light source may be employed for the two different methods. The two different methods may in this case be carried out simultaneously or sequentially in the device. The device may also comprise further analysis devices, in the form of spectrometers or based on other analysis methods.

The aforementioned laser optical devices (particularly in the form of microprobes) are based on there being a laser source which provides a monochromatic light source, their having an optical system for directing such a light beam onto the surface to be examined, and on their having an optical system for directing the light reflected or emitted by the surface onto a detector system, optionally with an analyzer of the intensity of the returning radiation as a function of the wavelength and/or frequency. Such a system may be combined with a further laser system for spatially resolved measurement of other properties of the surface, for example the surface structure.

According to another preferred embodiment, the laser optical device is guided over the surface in a systematic way which scans the surface, and the correspondingly spatially resolved data are processed to form a surface image. A surface image in connection with principles of the present invention is intended to mean a spatially resolved image of the nonmetallic chemical composition of the surface, or of the contaminations/coatings present thereon.

The data of a Raman spectrometer and those of a fluorescence spectrometer, or a combined Raman/fluorescence spectrometer, may in this case be processed in a combined/superimposed way in a processing unit to form a surface image.

The input radiation may be directed onto an area having an extent in the range of 10-100 μm in each spatial direction, and the radiation emitted by the surface may be collimated and/or filtered and/or amplified and/or focused and analyzed with respect to the frequencies and/or intensities contained therein, in order to generate the surface image.

As an alternative, it is also possible for the input radiation to be defocused onto an area having an extent in the range of 10-20 mm in each spatial direction.

Irradiation and/or extraction may be carried out with the aid of at least one optical fiber, in which case the same optical fiber may be used for irradiation and extraction.

Preferably, the surface is the surface of a turbine part, in particular a gas turbine part made of a metallic material, in particular made of a refractory material. The material has in this case preferably undergone a surface treatment selected from the group consisting of sandblasting, washing, etching, plasma treatment and a combination of such treatments, after the casting method and/or forging method, and the residues generated by these preparatory treatments, and optionally further contaminations, are identified and localized in a spatially resolved way. The material may likewise also have undergone a coating process (for example, it may be a turbine part on which a metallic bonding layer—generally referred to as a bond coat—for the formation of a thermal barrier layer has already been applied), this surface then being examined, in which case the aforementioned surface treatments may possibly also have been carried out after the coating process.

BRIEF DESCRIPTION OF THE DRAWINGS

Preferred embodiments of the invention will be described below with the aid of the drawing which merely serves for explanation and is not to be interpreted as restrictive. The single FIGURE (FIG. 1) shows a schematic structure of an exemplary device and method according to the invention, and a resulting graphical representation of the analysis.

DETAILED DESCRIPTION OF EXEMPLARY EMBODIMENTS

FIG. 1 schematically represents an exemplary method and components used therefor. A surface 6 is to be examined, which is either a part of a gas turbine that has undergone preparatory working steps as an unfinished casting part to prepare the surface for a coating process, for example to generate a metallic and/or ceramic layer, or is the surface of such a part from which such a layer previously present on the surface has been removed, the surface has been cleaned and processed, and a new layer is again to be applied.

There may be particulate contaminations 7, for example residues of a sandblasting process, i.e., grains used in this process which have remained on the surface. There may also be superficial residues 8, for example inorganic or organic substances which are for example residues of cleaning processes etc.

The device includes a monochromatic radiation source in the form of a laser 1. This laser directs a monochromatic laser beam 2 with a wavelength $\lambda_{in}$ onto the surface to be examined. This is done in a controlled way, i.e., the position of the laser over the surface is established by a device and the measurement is carried out as a function of this position.

The light beam strikes the surface, and the light is either reflected or absorbed, and re-emitted by the surface, specifically with a wavelength $\lambda_{out}$ longer than the wavelength $\lambda_{in}$ of the input radiation. In other words, the frequency of the emitted radiation is lower than the input frequency. This emitted light 3 in this case characterizes the contaminations 7, 8, since the frequency shift (or the wavelength shift) and/or the specific emission frequency (or the emission wavelength) are characteristic of the nature of the contamination. The position of the corresponding contamination is measured by keeping both the laser and a corresponding filter element 4, and a detector 5 placed behind them, in a targeted spatial position. Instead of a filter element 4, there may also be a collimator, a frequency filter or a lens, depending on the function which is required in connection with the examination method used.

The radiation detected by the detector 5 is subsequently transferred via a connection to a control unit or analysis unit 9. This control unit 9 also controls the laser 1, as well as the spatial position of these units. Accordingly, the control unit 9 controls the optical element in a scanning process over the surface and records the data as a function of the position of the optical components, and it generates a surface image 11 therefrom, optionally after corresponding data processing and filtering or averaging for noise suppression.

The surface image represented in FIG. 1 shows a corresponding example of such an image, on which residues of a sandblasting process are visible.

In connection with this general scheme, the surface contaminations may on the one hand be detected by Raman spectroscopy for the determination of contaminations and residues from the casting method.

Fluorescence spectroscopy may be used for the detection of aluminum oxide residues or residues from the casting method.

A system for carrying out the analysis may be configured to measure only one type of spectrum in a defined range, i.e., to detect only a very specific type of contamination, or both types may be examined in order to detect a plurality of different types of contaminations.

In principle, the optical system for the input light may, on the one hand, operate in a focused method. In this case, the laser beam is directed onto a small spot of typically no more than 10 to 100 micrometers in both spatial directions.

As an alternative, it is also possible to defocus the input light and illuminate a relatively large surface region with an extent of about 10 mm in both spatial directions. The beam returning to the spectrometer from the surface may be examined in the spectrometer either, again, only with respect to very specific wavelengths, or alternatively with respect to the entire spectrum, as a function of the position. If a large area is illuminated, then the spatial information may be obtained by correspondingly spatially resolved detection.

In principle, a first spectrometer may be used to acquire the fluorescence generated by aluminum oxide and a second spectrometer to acquire the Raman spectra of the surface being examined, the Raman spectrum being used for the determination of organic or inorganic contaminations on the surface.

Because of the low efficiency of the Raman effect (frequency shift), the two techniques may be used in two fully independent systems, the fluorescence measurement being used for the spatial resolution of aluminum oxide on the surface in the sense of a microscopy process, which then makes it possible to process the data in such a way that the size distribution of aluminum oxide particles, their spatial distribution, their shape and/or their thickness can be determined or imaged. The Raman signal may also be used merely to establish the presence or absence of contaminations on the surface to be examined.

Either the optical device may be displaced over a rigidly mounted holder of the part, in order to measure different surface regions, or it is also possible to keep the optical system spatially fixed and move the part relative to the optical device on a corresponding carriage. Particularly in connection with moving the optical system, it may also prove advantageous to use optical fibers which are guided on the surface or along the surface in a scanning process. In this case, the same optical fibers may be used to direct the input laser beam onto the surface and to guide the light returning from the surface to a detector.

In the scope of tests, it has been established that residues of a sandblasting method can in fact be mapped with a Raman microscope and a fluorescence microscope by using the proposed method. It was possible to obtain a surface image of a 4×4 mm surface section with a resolution of approximately 10 micrometers in a time of 90 minutes. FIG. 1 represents the corresponding optical image of the residues of a sandblasting process.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

We claim:

1. A method of spatially detecting the chemical composition of nonmetallic components on a surface which is subsequently to be coated with a metallic and/or ceramic and/or organic layer, the method comprising:
    providing a laser optical device;
    irradiating the surface with monochromatic irradiation at a first wavelength ($\lambda_{in}$) with said laser optical device;
    detecting radiation emitted by said surface at a second wavelength ($\lambda_{out}$) which is longer than the first wavelength ($\lambda_{in}$) with a detector such that the laser optical device and the detector are maintained at a targeted spatial position; and
    determining, based on said detecting, a spatial position of said nonmetallic components relative to at least one of said laser optical device and said detector.

2. The method as claimed in claim 1, wherein providing comprises providing a Raman spectrometer.

3. The method as claimed in claim 2, wherein detecting comprises determining organic and/or inorganic contaminations and/or residues on said surface with said Raman spectrometer.

4. The method as claimed in claim 1, wherein providing comprises providing a fluorescence spectrometer.

5. The method as claimed in claim 4, wherein detecting comprises determining the presence of aluminum oxide on the surface with said fluorescence spectrometer.

6. The method as claimed in claim 1, wherein providing comprises providing a Raman spectrometer and a fluorescence spectrometer.

7. The method as claimed in claim 6, wherein detecting comprises determining the presence of aluminum oxide on the surface with said fluorescence spectrometer.

8. The method as claimed in claim 1, wherein irradiating comprises systematically guiding the laser optical device over the surface, and further comprising:
    processing correspondingly spatially resolved data from said detecting to form a surface image.

9. The method as claimed in claim 8, wherein processing comprises processing data from a Raman spectrometer and from a fluorescence spectrometer, or from a combined Raman/fluorescence spectrometer, in a combined way to form a surface image.

10. The method as claimed in claim 1, wherein:
    irradiating comprises directing input radiation onto an area having a length in the range of 10-100 μm each spatial direction; and
    detecting comprises collimating and analyzing radiation emitted by the surface with respect to the frequencies and/or intensities contained in said radiation, in order to generate a surface image.

11. The method as claimed in claim 1, wherein:
    irradiating comprises defocusing said monochromatic irradiation onto an area having a length in the range of 1-20 mm in each spatial direction; and
    detecting comprises collimating and analyzing radiation emitted by the surface with respect to the frequencies and/or intensities contained in said radiation, in order to generate a surface image.

12. The method as claimed in claim 1, wherein:
    said laser optical device comprises at least one optical fiber; and
    said irradiating, said detecting, or both are carried out with said least one optical fiber.

13. The method as claimed in claim 12, wherein the same optical fiber is used for said irradiating and said detecting.

14. The method as claimed in claim 1, wherein the surface comprises the surface of a turbine part.

15. The method as claimed in claim 1, wherein the surface comprises the surface of a gas turbine part made of a metallic material.

16. The method as claimed in claim 1, wherein the surface comprises the surface of a gas turbine part made of a refractory material.

17. The method as claimed in claim 16, in which said gas turbine part has previously been cast or forged, and wherein the refractory material has previously undergone a surface treatment selected from the group consisting of sandblasting, washing, etching, plasma treatment, coating, and combinations thereof.

* * * * *